(12) United States Patent
Flores Gutierrez et al.

(10) Patent No.: US 11,609,220 B2
(45) Date of Patent: *Mar. 21, 2023

(54) METHOD AND APPARATUS FOR FAST-INITIALIZATION GAS CONCENTRATION MONITORING

(71) Applicant: Honeywell International Inc., Charlotte, NC (US)

(72) Inventors: Alfredo Flores Gutierrez, Southampton (GB); Keith Francis Edwin Pratt, Portsmouth (GB); Lamar Floyd Ricks, Westerville, OH (US)

(73) Assignee: Honeywell International Inc., Charlotte, NC (US)

( * ) Notice: Subject to any disclaimer, the term of this patent is extended or adjusted under 35 U.S.C. 154(b) by 2 days.

This patent is subject to a terminal disclaimer.

(21) Appl. No.: 17/249,481

(22) Filed: Mar. 3, 2021

(65) Prior Publication Data

US 2021/0247371 A1    Aug. 12, 2021

Related U.S. Application Data

(63) Continuation of application No. 16/787,704, filed on Feb. 11, 2020, now Pat. No. 10,962,517.

(51) Int. Cl.
*G01N 33/00* (2006.01)
*G01L 19/00* (2006.01)

(52) U.S. Cl.
CPC .......... *G01N 33/0073* (2013.01); *G01L 19/00* (2013.01)

(58) Field of Classification Search
CPC ........................... G01N 33/0073; G01L 19/00
USPC ........................................................ 73/23.2
See application file for complete search history.

(56) References Cited

U.S. PATENT DOCUMENTS

| 2010/0219960 A1 | 9/2010 | Moe et al. |
| 2014/0021064 A1 | 1/2014 | Pratt et al. |
| 2016/0077044 A1 | 3/2016 | Arkenberg et al. |
| 2016/0169704 A1 | 6/2016 | Badeja et al. |

(Continued)

FOREIGN PATENT DOCUMENTS

| DE | 3629483 A1 | 3/1988 |
| EP | 3431976 A1 | 1/2019 |
| WO | 2014/143175 A1 | 9/2014 |

OTHER PUBLICATIONS

Ex Parte Quayle Action Mailed on Sep. 17, 2020 for U.S. Appl. No. 16/787,704.

(Continued)

*Primary Examiner* — Nimeshkumar D Patel
*Assistant Examiner* — Jean F Morello
(74) *Attorney, Agent, or Firm* — Alston & Bird LLP

(57) ABSTRACT

A sensor assembly for monitoring gas concentration and a method of the same are provided. The sensor assembly includes a start-up sensor and a long-run sensor. The start-up sensor is characterized by a first power-on period and the long-run sensor is characterized by a second power-on period that is longer than the first power-on period. The sensor assembly also includes a controller in communication with the start-up sensor and the long-run sensor. The controller is configured to cause the start-up sensor and the long-run sensor to power on. The controller is further configured to power off the start-up sensor and monitor the gas concentration via the long-run sensor upon the expiration of the second power-on period. A corresponding method of monitoring gas concentration is also provided.

20 Claims, 6 Drawing Sheets

(56) References Cited

U.S. PATENT DOCUMENTS

2017/0276634 A1  9/2017  Saffell et al.
2018/0335411 A1  11/2018 Zanella, Sr. et al.
2020/0025701 A1  1/2020  Brown et al.

OTHER PUBLICATIONS

Extended European Search Report issued In European Application No. 21155096.7 dated Jul. 5, 2021, 9 pages.
Notice of Allowance and Fees Due (PTOL-85) dated Dec. 4, 2020 for U.S. Appl. No. 16/787,704.

METHOD AND APPARATUS FOR FAST-INITIALIZATION GAS CONCENTRATION MONITORING

CROSS-REFERENCE TO RELATED APPLICATIONS

This application is a continuation of and claims priority to U.S. patent application Ser. No. 16/787,704, filed Feb. 11, 2020, entitled "METHOD AND APPARATUS FOR FAST-INITIALIZATION GAS CONCENTRATION MONITORING," which is incorporated herein by reference in its entirety.

TECHNOLOGICAL FIELD

An example embodiment relates generally to a method and associated apparatus of gas monitoring and, more particularly, to a method and associated apparatus for fast-initializing gas concentration monitoring.

BACKGROUND

Modern gas sensors come in various forms, which may have large power consumption requirements or require extended initialization time to reach a steady-state of operation capable of generating accurate gas concentration measurements. Traditional oxygen sensors employed lead electrodes and consumed little to no power during operation. However, these lead-based oxygen concertation sensors had a limited useful life as the electrodes were consumed during operation. Moreover, lead-based devices, including these lead-based oxygen concentration sensors have been phased out of operation over time due to health concerns. Replacement technologies used for oxygen sensors are not limited by the same short usable life-spans as the original lead-based sensors, however these replacement technologies are characterized by relatively high levels of power consumption, which require these sensors to be connected to a continuous power supply or a relatively large on-board power supply (e.g., a battery) to enable use of the sensor over an extended period of time. Through applied effort, ingenuity, and innovation, many of these identified problems have been solved by the methods and apparatus of the present disclosure.

BRIEF SUMMARY

The illustrative embodiments of the present disclosure relate to fast-initialization gas concentration monitoring. In an example embodiment, a sensor assembly is provided for monitoring a gas concentration. The sensor assembly includes a start-up sensor and a long-run sensor. The start-up sensor is characterized by a first power-on period and the long-run sensor is characterized by a second power-on period that is longer than the first power-on period. The sensor assembly also includes a controller in communication with the start-up sensor and the long-run sensor. The controller is configured to cause the start-up sensor and the long-run sensor to power on. The controller is also configured to power off the start-up sensor and monitor the gas concentration via the long-run sensor upon the expiration of the second power-on period.

In some embodiments, the start-up sensor defines a start-up capillary size and the long-run sensor defines a long-run capillary size. In such embodiments, the start-up capillary size is larger than the long-run capillary size. In some embodiments, the second power-on period is from 10 minutes to 20 minutes. In some embodiments, the start-up sensor remains off until an instance in which the long-run sensor is powered off completely and restarted. In some embodiments, the start-up sensor and the long-run sensor are disposed within a single sensor housing.

In some embodiments, the start-up sensor and the long-run sensor are defined within a dual sensor. As such, the dual sensor defines a start-up electrode and a long-run electrode with a single counter electrode. In some embodiments, the start-up electrode is operable in association with a start-up capillary and the long-run electrode is operable in association with a long-run capillary. In some embodiments, the start-up sensor defines a start-up electrode and the long-run sensor defines a long-run electrode. In such embodiments, the start-up electrode is operable in association with a PTFE membrane having a first thickness and the long-run electrode is operable in association with a PTFE membrane having a second thickness greater than the first thickness. In some embodiments, the dual sensor is in communication with a controller configured switch between a dual powered state and a long-run state. In such embodiments, the dual powered state is characterized as an instance in which both the start-up sensor and the long-run sensor are powered and the long-run state is characterized as an instance in which the start-up sensor is powered off and the long-run sensor is powered on.

In some embodiments, the first power-on period is less than one minute. In some embodiments, an operating current of the start-up sensor is higher than an operating current of the long-run sensor. In some embodiments, the operating current of the start-up sensor is from 400 microamperes to 1000 microamperes and the operating current of the long-run sensor is from 50 microamperes to 200 microamperes. In some embodiments, at least one of the start-up sensor or the long-run sensor is an oxygen sensor or a partial pressure sensor. In some embodiments, the start-up sensor and the long-run sensor are two distinct sensors with distinct components in communication with the controller.

In an example embodiment, a method of monitoring a gas concentration is provided. The method includes powering on a start-up sensor and a long-run sensor. The start-up sensor is characterized by a first power-on period and the long-run sensor is characterized by a second power-on period that is longer than the first power-on period. The method also includes monitoring a gas concentration via the start-up sensor during the second power-on period of the long-run sensor. The method further includes powering off the start-up sensor and monitoring the gas concentration via the long-run sensor upon expiration of the second power-on period.

In some embodiments, the start-up sensor defines a start-up capillary size and the long-run sensor defines a long-run capillary size. In such an embodiment, the start-up capillary size is larger than the long-run capillary size. In some embodiments, the second power-on period is from 10 minutes to 20 minutes. In some embodiments, the start-up sensor remains off until an instance in which the long-run sensor is powered off completely and restarted. In some embodiments, the start-up sensor and the long-run sensor are disposed within a single sensor housing.

In some embodiments, the start-up sensor and the long-run sensor are defined within a dual sensor. In such an embodiment, the dual sensor defines a start-up electrode and a long-run electrode with a single counter electrode. In some embodiments, the start-up electrode is disposed near a start-up capillary and the long-run electrode is disposed near a long-run capillary. In some embodiments, the start-up sensor defines a start-up electrode and the long-run sensor defines a long-run electrode. In such an embodiment, the start-up electrode is operable in association with a PTFE membrane having a first thickness and the long-run electrode is operable in association with a PTFE membrane having a second thickness greater than the first thickness. In some embodiments, the dual sensor is in communication with a controller configured switch between a dual powered state and a long-run state. In such an embodiment, the dual powered state is characterized as an instance in which both the start-up sensor and the long-run sensor are powered and the long-run state is characterized as an instance in which the start-up sensor is powered off and the long-run sensor is powered on.

In some embodiments, the first power-on period is less than one minute. In some embodiments, an operating current of the start-up sensor is higher than an operating current of the long-run sensor. In some embodiments, the operating current of the start-up sensor is from 400 microamperes to 1000 microamperes and the operating current of the long-run sensor is from 50 microamperes to 200 microamperes. In some embodiments, at least one of the start-up sensor or the long-run sensor is an oxygen sensor or a partial pressure sensor. In some embodiments, the start-up sensor and the long-run sensor are two distinct sensors with distinct components in communication with a controller.

The above summary is provided merely for purposes of summarizing some example embodiments to provide a basic understanding of some aspects of the disclosure. Accordingly, it will be appreciated that the above-described embodiments are merely examples and should not be construed to narrow the scope or spirit of the disclosure in any way. It will be appreciated that the scope of the disclosure encompasses many potential embodiments in addition to those here summarized, some of which will be further described below.

BRIEF DESCRIPTION OF THE DRAWINGS

Figure 1:
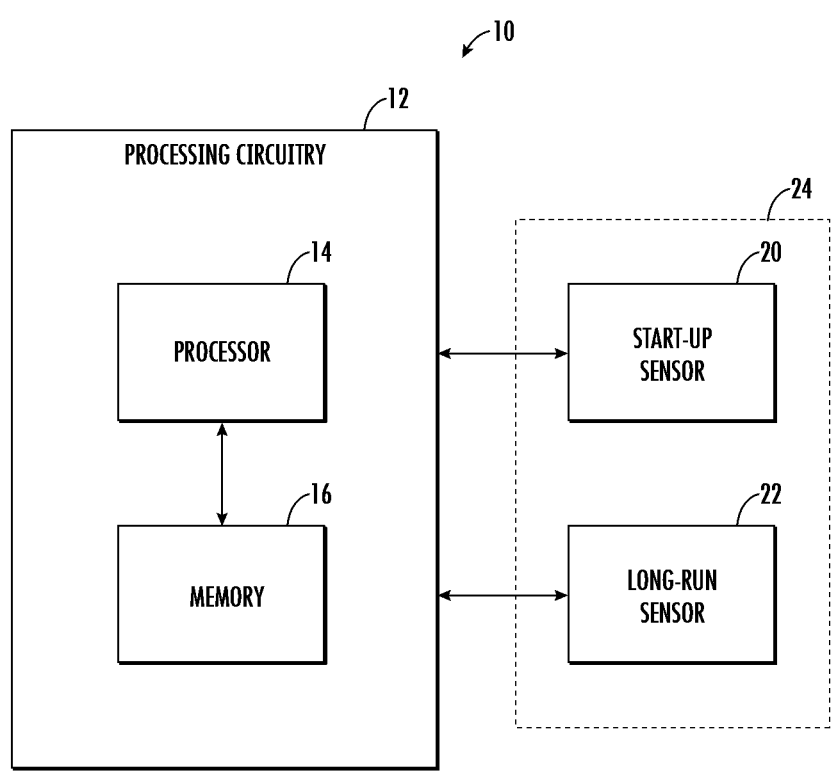
Figure 2:
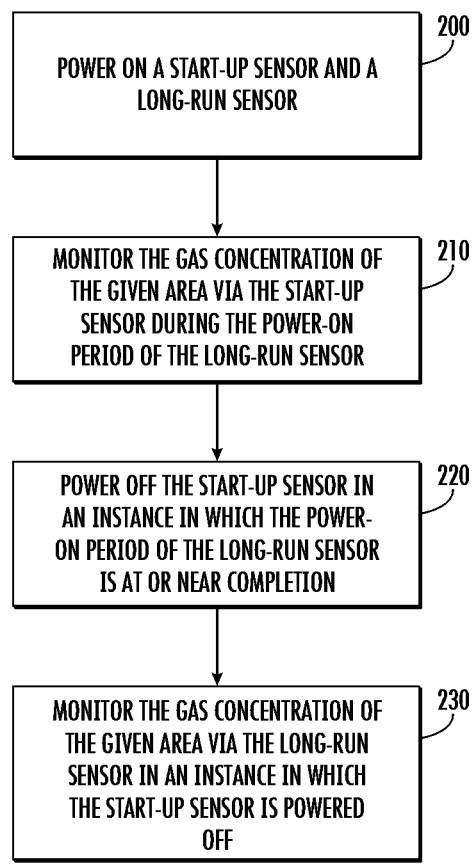
Figure 3:
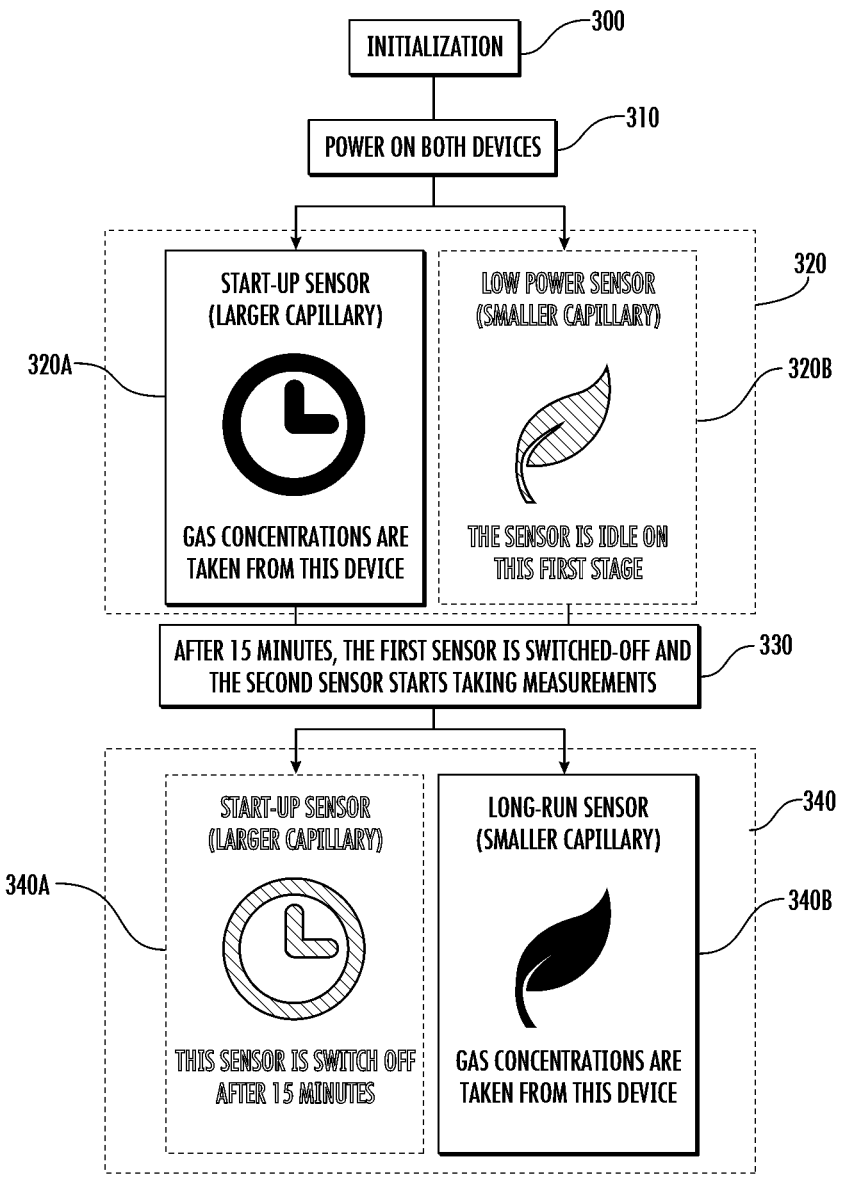
Figure 4A:
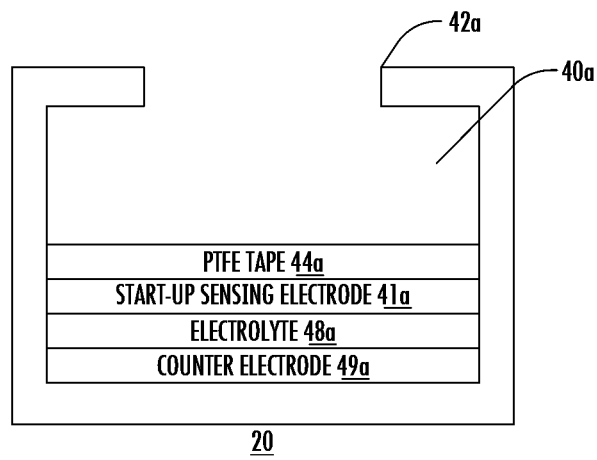
Figure 4B:
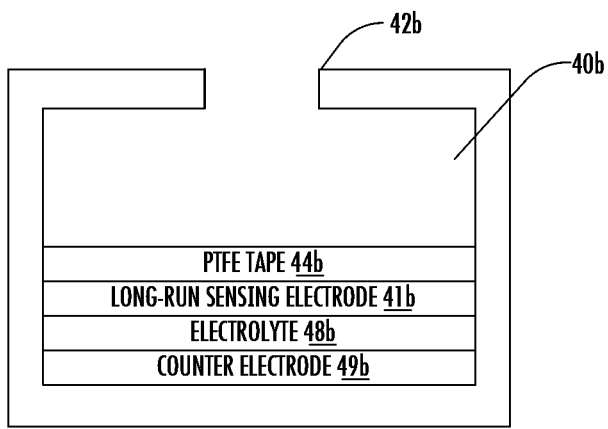
Figure 5:
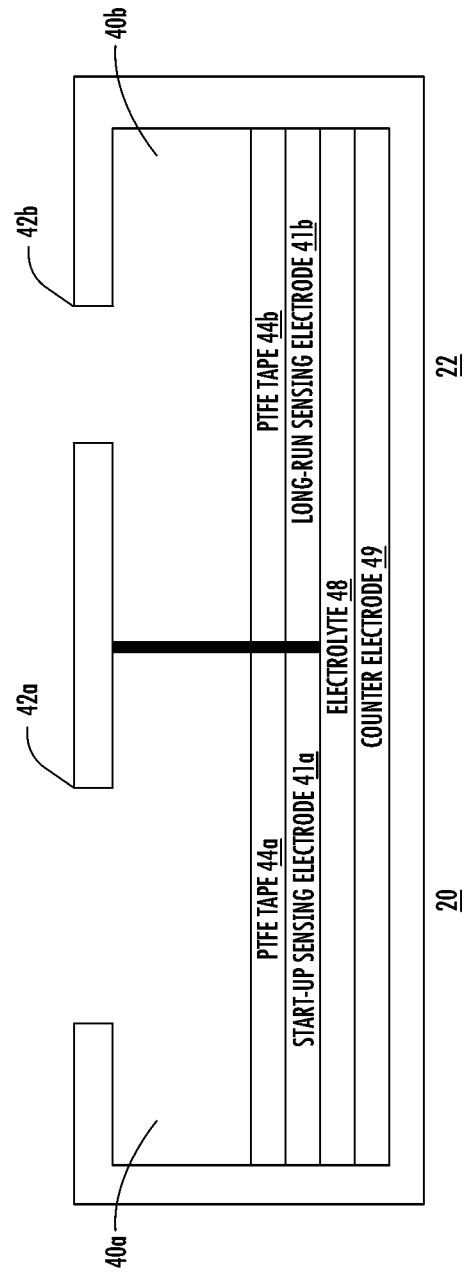
Figure 6A:
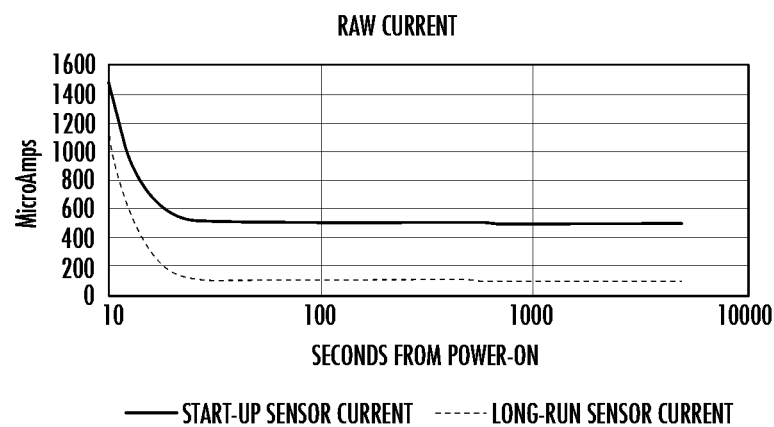
Figure 6B:
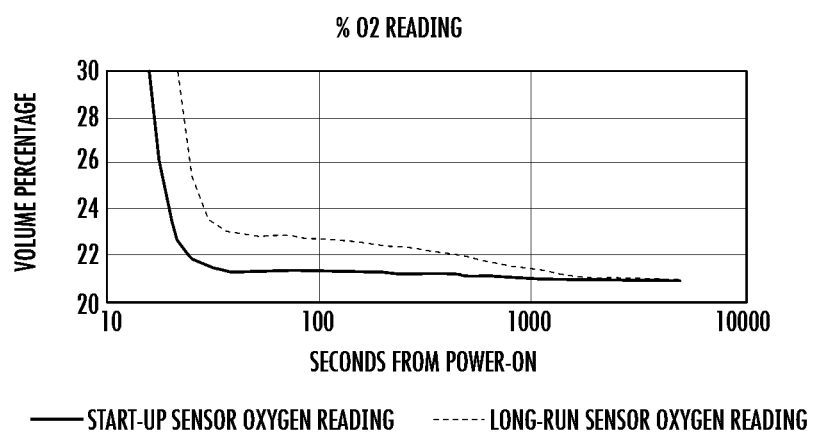

Having thus described certain example embodiments of the present disclosure in general terms, reference will hereinafter be made to the accompanying drawings, which are not necessarily drawn to scale, and wherein:

FIG. 1 is a block diagram of an apparatus configured in accordance with an example embodiment of the present disclosure;

FIG. 2 is a flowchart illustrating the operations performed, such as by the apparatus of FIG. 1, in accordance with an example embodiment of the present disclosure;

FIG. 3 is a further flowchart illustrating example operations of an apparatus in accordance with an example embodiment of the present disclosure;

FIGS. 4A and 4B are an example start-up sensor (FIG. 4A) and an example long-run sensor (FIG. 4B) in an instance in which the start-up sensor and the long-run sensor are distinct sensors;

FIG. 5 is an example dual sensor in an example embodiment in which the start-up sensor and the long-run sensor share a common housing with a common counter electrode;

FIG. 6A is a chart illustrating the current reading of an example start-up sensor and an example long-run sensor from the time the sensors are powered on until the power-on period of the long-run sensor is complete; and FIG. 6B is the oxygen concentration based on the current reading of the example start-up sensor and the example long-run sensor of FIG. 6A from the time the sensors are powered on until the power-on period of the long-run sensor is complete.

DETAILED DESCRIPTION

Some embodiments will now be described more fully hereinafter with reference to the accompanying drawings, in which some, but not all, embodiments are shown. Indeed, various embodiments may be embodied in many different forms and should not be construed as limited to the embodiments set forth herein; rather, these embodiments are provided so that this disclosure will satisfy applicable legal requirements. Like reference numerals refer to like elements throughout. As used herein, the terms "data," "content," "information," and similar terms may be used interchangeably to refer to data capable of being generated, processed, transmitted, received, and/or stored in accordance with embodiments of the present disclosure. Thus, use of any such terms should not be taken to limit the spirit and scope of embodiments of the present disclosure.

Various embodiments discussed herein allow for an energy efficient, fast initializing gas sensor apparatus characterized by a fast start-up sequence that enables the device to be easily and quickly changed between on and off configurations to conserve energy during periods of non-use, such that the apparatus may be powered-on quickly to begin generating accurate samples and without excessive energy usage during extended operating sessions.

Example Apparatus Configuration

FIG. 1 is a schematic diagram of an example apparatus configured for performing operations as described herein. Apparatus 10 is an example embodiment that may be embodied by or associated with any of a variety of computing devices that include or are otherwise associated with a device configured for providing advanced sensory features, which may include a sensor assembly 24. For example, apparatus 10 may be embodied as an oxygen concentration sensor configured for detecting the concentration of oxygen within a gaseous fluid (e.g., air).

The apparatus 10 may include, be associated with, or may otherwise be in communication with a communication interface (not shown), processor 14, a memory device 16, and a sensor assembly 24. In some embodiments, the processor 14 (and/or co-processors or any other processing circuitry assisting or otherwise associated with the processor) may be in communication with the memory device 16 (e.g., a non-transitory memory comprising one or more volatile and/or non-volatile memories). The memory device may be configured to store information, data, content, applications, instructions, or the like for enabling the apparatus to carry out various functions in accordance with an example embodiment of the present invention.

The processor 14 may be embodied in a number of different ways. For example, the processor may be embodied as one or more of various hardware processing means such as a coprocessor, a microprocessor, a controller, a digital signal processor (DSP), a processing element with or without an accompanying DSP, or various other processing circuitry including integrated circuits such as, for example, an ASIC (application specific integrated circuit), an FPGA (field programmable gate array), a microcontroller unit (MCU), a hardware accelerator, a special-purpose computer chip, or the like.

In an example embodiment, the processor 14 may be configured to execute instructions stored in the memory device 16 or otherwise accessible to the processor. Alternatively or additionally, the processor may be configured to execute hard coded functionality. As such, whether configured by hardware or software methods, or by a combination thereof, the processor may represent an entity (for example, physically embodied in circuitry) capable of performing operations according to an embodiment of the present invention while configured accordingly.

In various embodiments, the apparatus 10 additionally comprises a user interface element (not shown) comprising one or more of a display element (e.g., an LCD display, an LED display, a series of separately illuminating indicators, and/or the like), a sound-output device (e.g., providing audio-based indications of various functionalities of the device), and/or one or more input elements (e.g., a touch-screen device, a button array, and/or the like) for receiving user input for controlling various aspects of the operation of the apparatus (e.g., turning the apparatus on and/or off).

The apparatus 10 may include a sensor assembly 24, comprising a start-up sensor 20 and a long-run sensor 22. The start-up sensor 20 and the long-run sensor 22 may each be defined as a sensor capable of determining the gas concentration of one or more gases in a given area. As a specific example, each of the start-up sensor 20 and the long-run sensor 22 may comprise oxygen concentration sensors (e.g., oxygen pump sensors). In various embodiments, the start-up sensor 20 may be characterized as a fast-initialization, high-current consumption oxygen concentration sensor, and the long-run sensor 22 may be characterized as a slow-initialization, low-current consumption oxygen concentration sensor. In other words, the start-up sensor 20 may be capable of accurately monitoring gas concentration (e.g., oxygen concentration) faster than the long-run sensor 22 in an instance both the long-run sensor and the start-up sensor are powered on at substantially the same time. Said differently, the start-up sensor 20 is characterized by a first initialization period characterized between an instance in which the sensor is initialized and an instance in which the start-up sensor is capable of generating accurate oxygen concentration measurements, and the long-run sensor 22 is characterized by a second initialization period that is longer than the first initialization period. In various embodiments, the long-run sensor 22 may be configured to operate at a lower current than the start-up sensor 20, such that less power is required to operate the long-run sensor. Said differently, the start-up sensor 20 is characterized by a first rate of current consumption, and the long-run sensor 22 is characterized by a second rate of current consumption that is lower than the first rate of current consumption.

In various embodiments, the start-up sensor 20 may be a capillary limited oxygen sensor, a partial pressure oxygen sensor, or the like. In various embodiments, the start-up sensor 20 may be configured with a start-up sensing electrode 41a (shown in FIGS. 4A and 5) configured to determine the concentration (e.g., the oxygen concentration) of the gas present in the proximity of the sensing electrode. In an example embodiment, the gas concentration may be determined based on the current change of the sensor during operation (e.g., more oxygen results in a higher current). In various embodiments, in an instance in which power is not provided to the start-up sensor 20, the start-up sensing electrode may get swamped with gas such that the start-up sensor is not capable of producing an accurate gas concentration reading during an initial "power-on" period due to background current from the saturated target gas (e.g., oxygen). In various embodiments, in some embodiments, a limiting capillary may be defined on or near the start-up sensor 20 which limits the amount of gas around the sensor that can reach the start-up sensing electrode. The start-up capillary 42a may be built into the housing itself or may be an attachment. In various embodiments, the larger the capillary, the higher the current of the given sensor.

In various embodiments, the start-up sensor 20 defines a power-on period characterized as the period of time from the time the start-up sensor is powered on until the start-up sensor is capable of monitoring the gas concentration of a given area with sufficient accuracy. As discussed above, oxygen continues to flow into a sensor while the sensor is powered off (and the sensor is not consuming oxygen that has collected therein). Thus, immediately upon powering on the sensor, the sensor may detect an inflated concentration of oxygen during the power-on period while excess oxygen collected within the sensor is consumed. In certain embodiments, sensors characterized as having a higher current draw may consume this excess oxygen at similar rates as sensors characterized with relatively lower current draw, but the effect on the current as a percentage is less (e.g., higher current sensors are more resistant to background current). Over time, the excess oxygen collected within the sensor is consumed at a rate faster than new oxygen flows into the sensor, until the sensor reaches a steady-state operating condition, in which the flow of oxygen into the sensor at least substantially matches the rate of oxygen consumption by the sensor. During this steady-state operating condition, the oxygen concentration inboard of the capillary or diffusion limiting PTFE membrane within the sensor is substantially zero, such that all oxygen entering the sensor is being consumed at a diffusion limited rate, and accordingly the oxygen concentration measured by the sensor may be approximately an accurate concentration reading of the ambient environment. The duration of the power-on period may be at least substantially consistent for a given sensor configuration (for example, regardless of the length of time the sensor was powered off), and accordingly the duration of the power-on period may be consistent and defined within a start-up sequence of the sensor. In various embodiments, the duration of the power-on period, as well as a characterization of a sufficient level of accuracy to be attributed to a sensor (thereby determining when the sensor's readings can be assumed to be accurate) may be based on the sensor itself (e.g., a sensor may have different sensitivity and therefore different inherent accuracy). In various embodiments, the sufficient accuracy may be characterized as the point at which the start-up sensor begins accurately generating gas concentration data (e.g., whenever enough of the saturated oxygen within the sensor decays, such that the current reading is not greatly affected by the background current required to decay said oxygen). In some embodiments, the duration of the power-on period may be defined such that the operation of the start-up sensor 20 falls within the "deadband" of the oxygen reading, such that the oxygen reading based on the current is within 0.5% of the actual oxygen concentration. As noted, sensors characterized by a larger current draw are less sensitive to background current attributable to built-up excess oxygen within the sensor, and therefore such sensors are characterized as having a shorter-duration power-on period. In various embodiments, the power-on period may be approximated as may be a preset duration after the start-up sensor is initiated. In some embodiments, the preset duration may be approximated based on the assumption that the sensing electrode is fully saturated by the target gas (e.g., oxygen) when the sensor is powered on. In various embodiments, the preset time period may be set based on an understanding of the rate at which oxygen existing within the capillary is consumed by the sensor until a portion of or all of the "built up" oxygen is consumed in totality. In various embodiments, the start-up period may be approximated as a preset time period of approximately 30 seconds.

As discussed below, the power-on period of the start-up sensor 20 may be characterized as less than the power-on period of the long-run sensor 22. In various embodiments, the start-up sensor 20 may be configured to have a power-on period of less than one minute. For example, the power-on period for the start-up sensor 20 may be approximately 30 seconds. In various embodiments, the length of the power-on period of the start-up sensor 20 may be based on the operating current of the start-up sensor. In various embodiments, the higher current of the start-up sensor allows for the sensor to be initialized quicker in part due to a higher current being more resistant to background current. For example, the higher the operating current, the shorter the amount of time required to until the background current is sufficiently decreased to give an accurate current reading.

As just one non-limiting example, the operating current of the start-up sensor may be from approximately 400 microamperes to approximately 1000 microamperes. As another non-limiting example, the operating current of the start-up sensor may be from approximately 400 microamperes to approximately 800 microamperes. As another non-limiting example, the operating current of the start-up sensor may be from approximately 400 microamperes to approximately 600 microamperes. For example, the operating current of the start-up sensor may be from approximately 500 microamperes. In various embodiments, the operating current may be affected by the capillary size of the start-up sensor. In some embodiments, the start-up capillary 42a may be from approximately 40 to approximately 100 microns. For example, the start-up capillary 42a may be approximately 50 microns. As discussed herein, in some embodiments (e.g., in an instance in which the start-up sensor 20 is a partial pressure oxygen sensor), the start-up sensor 20 may not have a limiting capillary, but instead have a solid polytetrafluoroethylene (PTFE) membrane affecting the current therein.

In various embodiments, the long-run sensor 22 may be a capillary limited oxygen sensor, a partial pressure oxygen sensor, or the like. In various embodiments, the long-run sensor may be configured with a long-run sensing electrode 41b (as shown in FIGS. 4B and 5) configured to determine the concentration (e.g., the oxygen concentration) of the gas present in the proximity of the sensing electrode. In an example embodiment, the gas concentration may be determined based on the current change of the sensor during operation (e.g., more oxygen results in a higher current). In various embodiments, in an instance in which power is not provided to the long-run sensor 22, the long-run sensing electrode may get swamped with gas such that the long-run sensor is not capable of producing an accurate gas concentration reading during an initial "power-on" period. In various embodiments, a limiting capillary may be defined on or near the long-run sensor which limits the amount of gas around the sensor that can reach the start-up sensing electrode. The long-run capillary 42b may be built into the housing itself or may be an attachment. In various embodiments, the smaller the capillary, the lower the current draw of the given sensor.

In various embodiments, the long-run sensor may have a power-on period characterized as the period of time from the time the long-run sensor is powered on until the long-run sensor is capable of accurately monitoring the gas concentration of a given area with sufficient accuracy. As discussed above, oxygen continues to flow into a sensor while the sensor is powered off (and the sensor is not consuming oxygen that has collected therein). Thus, immediately upon powering on the sensor, the sensor may detect an inflated concentration of oxygen during the power-on period while excess oxygen collected within the sensor is consumed. In certain embodiments, sensors characterized as having a higher current draw may consume this excess oxygen at similar rates as sensors characterized with relatively lower current draw, but the effect on the current as a percentage is less (e.g., higher current sensors are more resistant to background current). Over time, the excess oxygen collected within the sensor is consumed at a rate faster than new oxygen flows into the sensor, until the sensor reaches a steady-state operating condition, in which the flow of oxygen into the sensor at least substantially matches the rate of oxygen consumption by the sensor. During this steady-state operating condition, the oxygen concentration inboard of the capillary or diffusion limiting PTFE membrane within the sensor is substantially zero, such that all oxygen entering the sensor is being consumed at a diffusion limited rate, and accordingly the oxygen concentration measured by the sensor may be approximately an accurate concentration reading of the ambient environment. The duration of the power-on period may be at least substantially consistent for a given sensor configuration (for example, regardless of the length of time the sensor was powered off), and accordingly the duration of the power-on period may be consistent and defined within a start-up sequence of the sensor. In various embodiments, the duration of the power-on period, as well as a characterization of a sufficient level of accuracy to be attributed to a sensor (thereby determining when the sensor's readings can be assumed to be accurate) may be based on the sensor itself (e.g., a sensor may have different sensitivity and therefore different inherent accuracy). In various embodiments, the sufficient accuracy may be characterized as the point at which the background current has decreased sufficiently in comparison to the operating current of the sensor (e.g., the point at which the transient start-up current due to the saturated oxygen, has decayed to a level where it is no longer significant compared to the steady state diffusion limited output current of the sensor). For example, to measure a signal to 1% accuracy, the transient background current must be less than 1% of the normal measurement current, such that, for example, a sensor with 100 microampere output (e.g., long-run sensor 22) in air would need a background current less than 1 microampere for 1% accuracy, whereas a sensor with 500 microampere output (e.g., start-up sensor 20) in air would give 1% accuracy with 5 microampere of background current. Due to the exponential decay of the background current, it may take much longer for the background signal to decay to 1 microampere than to 5 microampere (e.g., while the oxygen may decay at approximately the same rate in the start-up sensor 20 and the long-run sensor 22, the background current caused by said oxygen would interfere with the accuracy of the long-run sensor longer than the start-up sensor).

In various embodiments, the power-on period may be approximated to a preset duration after the long-run sensor 22 is initiated. In some embodiments, the preset duration may be approximated based on the assumption that the sensing electrode is fully saturated by the target gas (e.g., oxygen) when the sensor is powered on. In various embodiments, the preset duration may be defined based at least in part on an understanding of the rate at which oxygen existing within the capillary is consumed by the sensor until at least a portion of (e.g., all of) the "built up" oxygen is consumed in totality. In various embodiments, the power-on period of the long-run sensor 22 may be greater than the power-on period of the start-up sensor 20. In various embodiments, the long-run sensor may be configured to have a power-on period of approximately 10 minutes to 20 minutes. For example, the power-on period for the start-up period may approximately 15 minutes. In various embodiments, the length of the power-on period may be based on the operating current of the long-run sensor.

As the power-on period is defined to at least approximate the period of time to reach an equilibrium, steady-state condition within the sensor such that the concentration of oxygen within the sensor at least substantially matches the concentration of oxygen in an ambient environment surrounding the sensor, the capillary size (e.g., diameter) impacts the duration of the power-on period. Specifically, a larger capillary (e.g., larger diameter) has a corresponding larger diffusion-limited current response to oxygen, thereby rendering a transient background current attributable to the consumption of built-up oxygen within the sensor less relevant over time, which results in a shorter duration of time between the initialization of the sensor and a time instance in which the transient background current becomes sufficiently negligible that the sensor readings can be assumed to be an accurate representation of the oxygen concentration of the ambient environment. As such, the start-up sensor 20 is configured with a larger capillary than the long-run sensor 22, such that the start-up sensor has a shorter power-on period than the long-run sensor, but requires more current during operation. In various embodiments, the increased current allows for the start-up sensor 20 to be initialized quicker in part due to the larger capillary associated with the higher current sensors. As such, the background current caused by the oxygen that saturates the sensing electrode in an instance in which the sensor is powered off is a smaller percentage of the total current and therefore becomes non-statistically relevant more quickly than the long-run sensor having a comparatively smaller capillary (e.g., in an instance in which the current reading is within 0.5% of the exact current reading may be considered accurate). For example, the higher the operating current, then lower the power-on period. During the power-on period for the long-run sensor 22, the long-run sensor does not generate accurate oxygen concentration data (e.g., background current readings may impact the concentration readings during the power-on period), and accordingly the apparatus is configured to utilize data of the start-up sensor indicative of oxygen concentration data while the long-run sensor completes the start-up period.

In various embodiments, the operating current of the long-run sensor 22 may be less than the operating current of the start-up sensor 20. In various embodiments, the operating current of the long-run sensor 22 may be substantially less than the operating current of the start-up sensor 20. As just one non-limiting example, the operating current of the long-run sensor 22 may be from approximately 50 microamperes to approximately 200 microamperes. As another non-limiting example, the operating current of the long-run sensor 22 may be from approximately 75 microamperes to approximately 150 microamperes. For example, the operating current of the long-run sensor 22 may be approximately 100 microamperes. In various embodiments, the operating current may be affected by the capillary size of the long-run sensor. As such, the larger the capillary size, the higher the current of the associated sensor. For example, the start-up sensor 20 may have a higher current draw than the long-run sensor 22 due to the start-up sensor having a larger capillary than the long-run sensor. In various embodiments, the long-run capillary 42b may be from approximately 5 to approximately 15 microns. For example, the long-run capillary 42b may be approximately 10.5 microns. As discussed herein, in some embodiments (e.g., in an instance in which the long-run sensor 22 is a partial pressure oxygen sensor), the long-run sensor 22 may comprise a polytetrafluoroethylene (PTFE) membrane affecting the rate of oxygen diffusion (and therefore affecting the current draw of the sensor).

In various embodiments, the sensor assembly 24 may be configured as a single, dual sensor, such that the dual sensor has both the start-up sensing electrode 41a and the long-run sensing electrode 41b (e.g., different capillary feeds into each electrode), but a common counter electrode (e.g., as shown in FIG. 5). In various embodiments, the sensor assembly 24 may be two distinct sensors (e.g., both the start-up sensor 20 and the long-run sensor 22 are both attached to and in communication with the processing circuitry 12) as shown in FIGS. 4A and 4B. In various embodiments, the sensor assembly 24 may be two distinct sensors disposed within a common housing. Regardless of whether the sensor assembly 24 defines multiple individual sensors or a dual sensor, the sensor assembly 24 may be configured with a plurality of gas chambers 40a, 40b configured with the sensing electrodes therein. As such, the start-up sensor 20 may define the start-up capillary 42a, which allows the gas therein to enter the start-up gas chamber 40a. Additionally, the long-run sensor 22 may define the long-run capillary 42b, which allows the gas therein to enter the long-run gas chamber 40b. In various embodiments, the start-up capillary 42a may be larger than the long-run capillary 42b, such that the target gas can more easily reach the start-up sensing electrode 41a, resulting in a larger current for a given concentration of the target gas. As a result, the decaying background current of the start-up sensor 20 has relatively lesser effect on the measured signal than the impact of the decaying background current of the smaller output long-run sensor 22. Additionally, the sensor assembly 24 may be configured with one or more counter electrodes, which enables current to flow through the sensor, by driving a counter reaction. In various embodiments, the counter electrode may also be a reference electrode which is used to derive a stable reference voltage against which the sensing electrode is driven. In various embodiments, the one or more reference electrodes may be provided independent of the counter electrode. For example, in an instance in which the start-up sensor 20 and the long-run sensor 22 are distinct sensor, then each may have a distinct counter electrode and a distinct reference electrode, while in an instance in which the start-up sensor 20 and the long-run sensor 22 are in the same housing (e.g., FIG. 5), then there may be a distinct counter electrode and a distinct reference electrode for use with each sensing electrode). In some embodiments, each of the start-up electrode 41a and long-run electrode 41b may be associated with separate, distinct counter electrodes 49a, 49b (e.g., in an instance multiple distinct sensors are provided as shown in FIGS. 4A and 4B). Alternatively, the start-up electrode 41a and the long-run electrode 41b may share the same counter electrode 49 (as shown in FIG. 5). In such an embodiment, the start-up sensor 20 and the long-run sensor 22 may share the same electrolyte 48. Alternatively, in some instances, such as when the start-up sensor 20 and the long-run sensor 22 are separate sensors, the start-up sensor 20 may have distinct electrolyte 48a and the long-run sensor 22 may have distinct electrolyte 48b, as shown in FIGS. 4A and 4B. In various embodiments, the sensing electrodes 41a, 41b may use PTFE tape 44a, 44b. In various embodiments, one or both of the PTFE tape 44a, 44b may be porous (e.g., in the case of capillary limited oxygen sensors), or one or both of the PTFE tape 44a, 44b may be a solid PTFE tape (e.g., in the case of partial pressure oxygen sensors where the tape itself is the diffusion limiter). In some embodiments, the PTFE tape 44a, 44b may be different types of tape (e.g., one sensor may have a porous PTFE tape, while the other may have a solid PTFE tape). In various embodiments, wherein one or both of the sensors are partial pressure sensors, the given partial pressure sensor may be configured without a capillary, such that the diffusion limitation (sensitivity) is determined by a solid PTFE membrane. For example, a thicker PTFE membrane results in a smaller current. As such, the long-run sensor may have a thicker solid PTFE membrane than the start-up sensor in an instance in which both of the sensors are partial pressure sensors.

Referring now to FIG. 2, an example embodiment of the present disclosure includes a flow diagram for the processing circuitry 12, the processor 14, the sensor assembly 24, or the like, to monitor gas concentration in an energy efficient manner. Various embodiments of the present disclosure allow for the sensor assembly 24 to be powered off during periods without the need for long initializing time for the sensor. Various embodiments of the present disclosure allows for monitoring gas concentration to begin shortly after the sensor assembly is powered on without consuming high amounts of power during the long-term operation.

Referring now to Block 200 of FIG. 2, the method of monitoring gas concentration includes powering on a start-up sensor and a long-run sensor. In some embodiments, the start-up sensor 20 and the long-run sensor 22 may be powered on at substantially the same time. As discussed above, both the start-up sensor 20 and the long-run sensor 22 may each have a power-on period characterized as a period of time for each sensor to be capable of monitoring gas concentration of a given area with sufficient accuracy. In various embodiments, in an instance the sensor assembly 24 (e.g., a start-up sensor 20 and/or a long-run sensor 22) is powered off (e.g., no current is received by the sensor), ambient gas may be received by the sensing electrode, causing inaccurate initial readings once a given sensor is powered on (e.g., a sufficient amount of current must pass through the sensor to removing built up target gas from the electrolyte and within the vicinity of the sensing electrode before the sensor generates accurate data). In various embodiments, a smaller capillary entry for a sensor may allow for a shorter power-on period due to a higher operating current being more resistant to background current. In various embodiments, the start-up sensor 20 may be configured with a larger capillary than the long-run sensor 22, such that the start-up sensor may require a higher operating current than the long-run sensor, but a shorter power-on period than the long-run sensor.

Referring now to Block 210 of FIG. 2, the method includes monitoring the gas concentration of the given area via the start-up sensor 20 during the power-on period of the long-run sensor 22. In various embodiments, the start-up sensor 20 may be configured to have a relatively short power-on period, such that the start-up sensor is capable of accurately monitoring the gas concentration of the given area quickly after being powered on. In various embodiments, the start-up sensor 20 may have a shorter power-on period than the long-run sensor 22. In various embodiments, the start-up sensor may have a substantially shorter power-on period than the long-run sensor. For example, the start-up sensor may be capable of monitoring the gas concentration within a minute of powering on (e.g., approximately 30 seconds), while the long-run sensor may take upwards of fifteen minutes to be capable of monitoring the gas concentration.

Referring now to Block 220 of FIG. 2, the method includes powering off the start-up sensor 20 in an instance in which the power-on period of the long-run sensor 22 is at or near completion. In various embodiments, the apparatus 10 may be configured to allow for continuous monitoring of the gas concentration, such that the start-up sensor continues operating concurrently with the long-run sensor for at least a period of time after the power-on period of the long-run sensor is complete. In various embodiments, the start-up sensor may be powered off shortly before the power-on period of the long-run sensor is complete. In various embodiments, the start-up sensor may be powered off at substantially the same time that the power-on period of the long-run sensor has be completed, such that there is continuous monitoring with minimal excess energy usage. In some embodiments, there may be an instance in which the power-on period of the start-up sensor 20 and the power-on period of the long-run sensor 22 may be completed and both the sensors may continue to be powered for at least a short amount time (e.g., to check whether the output of the long-run sensor is sufficiently stable to turn off the start-up sensor 20, since the output of the start-up sensor 20 may be more stable at or near the time the power-on period of the long-run sensor is complete). In various embodiments, the start-up sensor 20 may be used to confirm that the long-run sensor 22 can accurately monitor the gas. In some embodiments, power may be conserved by actively adjusting the power-on time of the start-up sensor 20.

Referring now to Block 230 of FIG. 2, the method includes monitoring the gas concentration of the given area via the long-run sensor 22 in an instance in which the start-up sensor 20 is powered off. In various embodiments, in an instance in which the power-on period of the long-run sensor 22 is complete, the long-run sensor may be capable of accurately monitoring the gas concentration of the given area using less power than the start-up sensor 20 required. In various embodiments, the long-run sensor 22 may operate until the apparatus 10 is powered off (e.g., the apparatus 10 may be powered off during night times). In an instance in which the apparatus 10 is powered off, when the apparatus is then powered back on, the operations may begin back at Block 200 (e.g., both the start-up sensor 20 and the long-run sensor 22 are powered and the power-on period of each begins).

FIG. 3 illustrates an illustrative flowchart of an example apparatus operation in accordance with an example embodiment. The operations discussed herein coordinate with the operations of FIG. 2. In various embodiments, the operations may be carried out via the processing circuitry 12, the sensor assembly 24, or the like. Referring now to Blocks 300 and 310 of FIG. 3, in an instance in which the apparatus 10 is powered off, the apparatus 10 may be initialized and as a part of this initialization, both the start-up sensor 20 and the long-run sensor 22 may be powered on. In various embodiments, as discussed above, once the power-on period of the start-up sensor 20 has been completed (e.g., typically less than one minute), the operations of Block 320 are occurring. As shown, the start-up sensor 20 operates normally by monitoring the gas concentration (e.g., shown in Block 320A), while the long-run sensor 22 continues the power-on period (e.g., as shown in Block 320B, the long-run sensor may be powered, but does not produce accurate gas concentrations due to background current). In various embodiment, after a set period of time (e.g., as shown in Block 330), the start-up sensor 20 may be powered off and the long-run sensor 22 may monitor the gas concentration. In various embodiments, the set period of time may be based on the power-on period of the long-run sensor. For example, in an instance the power-on period of the long-run sensor is approximately 15 minutes, the set period of time may be at or near 15 minutes, as shown. Block 340 of FIG. 3 illustrates the long-run state of the apparatus 10, such that the long-run sensor (e.g., shown in Block 340B) monitors the gas concentration and the start-up sensor is powered off (e.g., shown in Block 340A).

FIG. 6A illustrates an example current reading of a 500 microampere start-up sensor 20 and a 100 microampere long-run sensor 22 in an instance in which the sensors are powered on at approximately the same time and the oxygen concentration is held constant at approximately 20.9%. As shown, the current of the start-up sensor 20 and the long-run sensor 22 both decreases as time passes as the target gas saturating the sensing electrode (e.g., oxygen) is consumed until the current is approximately the sensor signal plus any additional current caused by the actual target gas concentration. As shown in the illustrated embodiment, the changes in current are approximately the same for both sensors, but the percentage change in current of the start-up sensor 20 is lower than the percentage change in current of the long-run sensor 22. As such, the oxygen readings shown in FIG. 6B normalizes towards the actual oxygen concentration quicker for the start-up sensor 20 than the long-run sensor 22.

FIG. 6B illustrates the effect of the lower current of the long-run sensor 22 on the oxygen concentration reading. As shown, the oxygen concentration reading from both sensors begin substantially higher than the 20.9% oxygen concentration due to the background current caused by the saturated target gas from the powered-off period. As the saturated target gas (e.g., oxygen) is consumed by both sensors (e.g., at approximately the same rate), the start-up sensor 20 normalizes towards the 20.9% oxygen concentration reading quicker than the long-run sensor 22. For example, the oxygen reading of the start-up sensor 20 normalizes to within 0.5% of the oxygen concentration at approximately 30 seconds (e.g., the power-on period of the start-up sensor), while the oxygen reading of the long-run sensor 22 normalizes to within 0.5% of the oxygen concentration much later (e.g., the power-on period of the long-run sensor may be approximately 15 minutes). As discussed herein, the start-up sensor 20 may be powered off in an instance in which the long-run sensor 22 has normalized to within 0.5% of the oxygen concentration.

Various embodiments discussed herein allow for an energy efficient, fast initializing gas sensor apparatus that allows the apparatus to be powered off during non-use periods to conserve energy, while also allowing for quick powering on of the apparatus without excessive energy usage during extended operating sessions.

As described above, FIGS. 2 and 3 illustrate flowcharts of various aspects of an apparatus 10 and method according to example embodiments of the invention. It will be understood that each block of the flowchart, and combinations of blocks in the flowchart, may be implemented by various means, such as hardware, firmware, processor, circuitry, and/or other devices associated with execution of software including one or more computer program instructions. For example, one or more of the procedures described above may be embodied by computer program instructions stored and executable via the memory of the apparatus.

Blocks of the flowchart support combinations of means for performing the specified functions and combinations of operations for performing the specified functions for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In some embodiments, certain ones of the operations above may be modified or further amplified. Furthermore, in some embodiments, additional optional operations may be included. Modifications, additions, or amplifications to the operations above may be performed in any order and in any combination.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A sensor assembly for monitoring a gas concentration, the sensor assembly comprising:
    a start-up sensor and a long-run sensor, wherein the start-up sensor is characterized by a first power-on period of less than one minute and the long-run sensor is characterized by a second power-on period that is longer than the first power-on period; and
    a controller in communication with the start-up sensor and the long-run sensor, the controller configured to cause the start-up sensor and the long-run sensor to power on at a same time and the controller is further configured to power off the start-up sensor and monitor the gas concentration via the long-run sensor upon the expiration of the second power-on period.

2. The sensor assembly of claim 1, wherein the start-up sensor defines a start-up capillary size and the long-run sensor defines a long-run capillary size, and wherein the start-up capillary size is larger than the long-run capillary size.

3. The sensor assembly of claim 1, wherein the second power-on period is 15 minutes.

4. The sensor assembly of claim 1, wherein the start-up sensor remains off until an instance the long-run sensor is powered off completely and restarted.

5. The sensor assembly of claim 1, wherein the start-up sensor and the long-run sensor are disposed within a single sensor housing.

6. The sensor assembly of claim 1, wherein the start-up sensor and the long-run sensor are defined within a dual sensor, wherein the dual sensor defines a start-up electrode and a long-run electrode with a single counter electrode.

7. The sensor assembly of claim 1, wherein the start-up sensor defines a start-up electrode and the long-run sensor defines a long-run electrode, wherein the start-up electrode is operable in association with a PTFE membrane having a first thickness and the long-run electrode is operable in association with a PTFE membrane having a second thickness greater than the first thickness.

8. The sensor assembly of claim 6, wherein the dual sensor is in communication with a controller configured switch between a dual powered state and a long-run state, wherein the dual powered state is characterized as an instance in which both the start-up sensor and the long-run sensor are powered and the long-run state is characterized as an instance in which the start-up sensor is powered off and the long-run sensor is powered.

9. The sensor assembly of claim 1, wherein an operating current of the start-up sensor is higher than an operating current of the long-run sensor.

10. The sensor assembly of claim 1, wherein at least one of the start-up sensor or the long-run sensor is an oxygen sensor or a partial pressure sensor.

11. A method of monitoring a gas concentration, the method comprising:
    powering on a start-up sensor and a long-run sensor at a same time, wherein the start-up sensor is characterized by a first power-on period of less than one minute and the long-run sensor is characterized by a second power-on period that is longer than the first power-on period;
    during the second power-on period of the long-run sensor, monitoring the gas concentration via the start-up sensor; and
    upon expiration of the second power-on period, powering off the start-up sensor and monitoring the gas concentration via the long-run sensor.

12. The method of claim 11, wherein the start-up sensor defines a start-up capillary size and the long-run sensor defines a long-run capillary size, and wherein the start-up capillary size is larger than the long-run capillary size.

13. The method of claim 11, wherein the second power-on period is 15 minutes.

14. The method of claim 11, wherein the start-up sensor remains off until an instance the long-run sensor is powered off completely and restarted.

15. The method of claim 11, wherein the start-up sensor and the long-run sensor are disposed within a single sensor housing.

16. The method of claim 11, wherein the start-up sensor and the long-run sensor are defined within a dual sensor, wherein the dual sensor defines a start-up electrode and a long-run electrode with a single counter electrode.

17. The method of claim 11, wherein the start-up sensor defines a start-up electrode and the long-run sensor defines a long-run electrode, wherein the start-up electrode is operable in association with a PTFE membrane having a first thickness and the long-run electrode is operable in association with a PTFE membrane having a second thickness greater than the first thickness.

18. The method of claim 16, wherein the dual sensor is in communication with a controller configured switch between a dual powered state and a long-run state, wherein the dual powered state is characterized as an instance in which both the start-up sensor and the long-run sensor are powered and the long-run state is characterized as an instance in which the start-up sensor is powered off and the long-run sensor is powered.

19. The method of claim 11, wherein an operating current of the start-up sensor is higher than an operating current of the long-run sensor.

20. The method of claim 11, wherein at least one of the start-up sensor or the long-run sensor is an oxygen sensor or a partial pressure sensor.

* * * * *